United States Patent [19]
Desjardins

[11] Patent Number: 5,972,622
[45] Date of Patent: Oct. 26, 1999

[54] METHOD OF DETECTING APOPTOSIS USING AN ANTI-HUMAN GP46 MONOCLONAL ANTI-BODY

[76] Inventor: Louise Desjardins, 1139 St. Jovite Ridge, Gloucester, Ontario, Canada, K1C 1Y6

[21] Appl. No.: 08/796,841

[22] Filed: Feb. 6, 1997

Related U.S. Application Data

[60] Provisional application No. 60/011,324, Feb. 8, 1996.
[51] Int. Cl.$^6$ ................ G01N 33/532; G01N 33/567; G01N 33/534
[52] U.S. Cl. ................ 435/7.1; 436/503; 436/504; 436/507; 436/544; 436/545; 436/546; 436/547; 436/512; 435/7.21
[58] Field of Search ................ 435/7.1, 7.21; 436/507, 503, 504, 544, 545, 546, 547, 512

[56] References Cited

PUBLICATIONS

Tanaka et al Int. Journal of Cancer (Oct. 15, 1990) vol. 46(4) pp. 675–681.

*Primary Examiner*—Paula K. Hutzell
*Assistant Examiner*—Geetha P. Bansal
*Attorney, Agent, or Firm*—Sterne, Kessler, Goldstein & Fox P.L.L.C.

[57] ABSTRACT

This invention relates to antibodies or fragments thereof that can be used as indicators of apoptosis. More specifically, this invention relates to antibodies and fragments thereof that selectively bind GP46, a protein whose levels increase significantly upon induction of apoptosis. This invention also relates to the hybridomas that produce anti-GP46 monoclonal antibodies. This invention also discloses a method of detecting cell death by apoptosis in vitro or in vivo by detecting and quantifying GP46 present in biological samples, comprising contacting the sample with the antibodies or fragments to form GP46 immunocomplexes, which may then be detected by the use of known methods. This detection method is useful for research into apoptosis and research relating to diseases in which apoptosis is involved. This method could also be used to diagnose the extent of damage caused by a particular disease or to evaluate the efficacy of drug treatments. The present invention also relates to a method of using the anti-GP46 antibodies or fragments in nuclear medical imaging. The present invention further relates to therapeutic uses of the anti-GP46 antibodies or fragments. The antibodies or fragments can also be incorporated into kits for the detection of apoptosis.

15 Claims, 4 Drawing Sheets

METHOD OF DETECTING APOPTOSIS USING AN ANTI-HUMAN GP46 MONOCLONAL ANTI-BODY

This application claims benefits of provisional application 60/011,324 filed Feb. 8, 1996.

FIELD OF THE INVENTION

The present invention relates to the use of anti-GP46 antibodies or fragments thereof as specific, and versatile indicators of cell death by apoptosis. These antibodies can be used for research into apoptosis, for diagnosis of apoptosis, to monitor and evaluate the efficacy of a medical treatment, as targeting moieties to direct therapeutic drugs to apoptotic cells, and in therapeutic applications for the treatment of diseases involving apoptosis.

BACKGROUND OF THE INVENTION

Apoptosis is programmed cell death, a naturally occurring process involved in both the development and aging of cells. It is the process whereby the body can rid itself of unwanted, old, or damaged cells. Apoptosis is the physiological counterpart of cell proliferation. It is essential for both biological processes such as normal tissue turnover, embryonic development, and maturation of the immune system, including pathological processes, such as hormone deprivation, thermal stress and metabolic stress. (Wyllie, A. H., in Bowen and Lockshin (eds.) *Cell Death in Biology and Pathology* (Chapman and Hall, 1981), at 9–34).

Apoptosis is characterized by a decrease in cell volume, a condensation of chromatin, cellular budding, and the fragmentation of DNA into a ladder of 180 base pair (bp) oligomers with 3'-OH free ends, a hallmark of apoptosis. Cell membranes maintain their integrity through the process, and lysosomes remain intact. There is no inflammatory response from apoptosis. Affected cells undergo phagocytosis by adjacent normal cells and by some macrophages.

The biochemical effector pathways that underlie the apoptotic mechanisms are as yet unknown. It has been suggested that the apoptotic mechanism involves one or more $Ca^{2+}/Mg^{2+}$-dependent endogenous endonucleases (Arends et al., (1990) *Am. J. Pathol.* 136:593–608); transglutaminase activity (Fesus et al., (1987) *FEBS Lett.* 224:104–108; Taress et al., (1992) *J. Biol. Chem. Cell* 75:653–660); and the generation of oxygen radicals (Hockenberry et al., (1993) *Cell* 75:241–251; Butke and Sandstrom (1994) *Immun. Today* 15:7–10). It appears that gene expression is required for apoptosis as this process can be stopped by inhibitors of RNA or protein synthesis (Martin et al., *J. Cell Biol.* 106:829–844 (1988)).

Although the apoptotic mechanism has not been determined, several proto-oncogenes, including c-myo, p53, and bol-2, have been implicated in its control (See Grand et al., (1995) *Exp. Cell Res.* 218:439–451). The delicate balance between these genes determines whether a cell will underto apoptosis or survive. None of these gene products, however, have been identified as a specific marker for apoptosis because these genes are involved in other biochemical processes.

Apoptosis can be activated by a number of intrinsic or extrinsic signals. These signals include the following: mild physical signals, such as ionization radiation, ultraviolet radiation, or hyperthermia; low to medium doses of toxic compounds, such as azides or hydrogen peroxides; chemotherapeutic drugs, such as etoposides and teniposides, cytokines such as tumour necrosis factors and transforming growth factors; and stimulation of T-cell receptors.

When apoptosis is unregulated, disease results. Unregulated apoptosis is involved in diseases such as cancer, heart disease, neurodegenerative disorders, autoimmune disorders, and viral and bacterial infections. Cancer, for example, not only triggers cells to proliferate but also blocks apoptosis. Cancer is partly a failure of apoptosis: the orders for the cells to kill themselves by apoptosis are blocked. New cancer treatments that involve inducing apoptosis are being researched.

Disease and shock can cause cardiac cells to induce apoptosis. For example, cells deprived of oxygen after a heart attack release signals that induce apoptosis in cells in the heart. New treatments involving apoptosis blockers are being developed.

Apoptosis may also be involved in the destruction of neurons in people afflicted by strokes or neurodegenerative diseases such as Alzheimer's disease, Parkinson's disease, and ALS (Lou Gehrig's disease). There is evidence suggesting that ischemia can kill neurons by inducing apoptosis. It has been shown that neurons that are resistant to apoptosis are also resistant to ischemic damage, thus, inhibition of apoptosis may be a therapeutic strategy for the treatment of neurodegenerative disorders such as stroke.

A failure of apoptosis in the immune system can lead to autoimmune diseases. T-cells differentiate between self and nonself (foreign) cells in the body. Autoimmune diseases such as rheumatoid arthritis, diabetes, and multiple sclerosis, result when a small percentage of T-cells attack the body's own tissue. Drugs are being developed that induce apoptosis in these T-cells.

Evidence also suggests that AIDs develops when the human immunodeficiency virus (HIV) sets off unregulated and untimely apoptosis in CD-4 and CD-8 cells, the defenders of the immune system.

There is an enormous therapeutic potential in controlling apoptosis in these diseases. Much research is now focussing on developing drugs that can either inhibit or induce apoptosis depending on the targeted disease. A major difficulty with researching apoptosis and drugs to control it is that a reliable marker of apoptosis has not yet been developed.

A marker is also needed in order to determine whether cells are dying or have been killed by apoptosis in the diagnosis of these diseases. For example, a marker for apoptosis could be used to determine the extend of neuronal damage caused by a stroke.

Apoptosis drugs are being used in therapy, and a reliable marker is needed in order to evaluate the progress of the therapy. For example, a major goal of some cancer chemotherapies has become to kill cancer cells by inducing apoptosis in these cells. It is estimated, however, that 45 percent of cancer drug treatments fail. It would be useful to have a method to assess the performance of new treatments in a reliable and effective manner. Currently, oncologists have to rely on manual measurements of tumour size and CAT Scan technologies to provide treatment feedback. The former is labour intensive while the latter is very expensive. In addition, both methods require at least one month of treatment to be effective. Furthermore, these methods do not indicate the nature of biochemical activities in the tumour. As such, there is a need for markers of apoptosis in order to determine whether apoptosis has been induced in tumour cells by the cancer chemotherapy.

Apoptosis is one type of cell death, another is necrosis. Cell death by necrosis often interferes with a determination of whether apoptosis has been induced. There are, however, distinguishing characteristics between the two. In contrast to apoptosis, necrosis is not genetically controlled, rather, it is induced by severe environmental trauma, such as chronic doses of heavy metals, chemicals, or extreme heat. The cells have little or no time to respond to the environmental stress and therefore die. Since RNA and protein synthesis are not required in order for cell death to occur, necrosis cannot be inhibited by drugs.

Necrosis is characterized by the swelling and rupturing of cells, the loss of membrane integrity, a random breakdown of DNA into fragments of variable size, and the phagocytosis of cellular debris by macrophages. The release of lysosomal enzymes damages neighbouring cells, thus, cells die in groups. This produces an inflammatory response in tissue. Cell death by necrosis involves no direct RNA or protein synthesis.

The differences in characteristics between apoptosis and necrosis allow one to differentiate between cell death by apoptosis and cell death by necrosis based on the following combinations of characteristics, apoptosis involves RNA and protein synthesis, the production of laddered DNA fragments, the maintenance of membrane integrity, and the exclusion of vital dyes during the process of dying by apoptosis; necrosis involves no RNA or protein synthesis, the production of random DNA fragments, the absence of membrane integrity, and the retention of vital dyes.

Despite the notable differences between apoptosis and necrosis, many long and tedious procedures are required to determine by which mechanism cell death has occurred. These procedures do not identify whether apoptosis is starting or is ongoing in a cell, this causes uncertainty in research, in the development of drugs that induce or inhibit apoptosis, in diagnosis, and in medical treatment. To date, a reliable marker for the early detection of apoptosis does not exist.

To date, a reliable marker for the early detection of apoptosis does not exist. Currently, the marker most commonly used to detect apoptosis is TUNEL labeling of the 3'-OH free end of DNA fragments produced during apoptosis (Gavrieli, Y. et al. (1992) *J. Cell Bio.* 119:493). The TUNEL method consists of catalytically adding a nucleotide, which has been conjugated to a chromogen system or a to a fluorescent tag, to the 3'-OH end of the 180-bp oligomer DNA fragments in order to detect the fragments. The presence of a DNA ladder of 180-bp oligomers is indicative of apoptosis.

Procedures to detect cell death based on the TUNEL method are offered by both Boehringer Mannheim (Cell Death Kit) and Oncor (Apoptag Plus). This method involves a number of limitations. Early detection of apoptosis is not possible with this method because the DNA ladder is an end-point in the apoptosis pathway. Also, although the TUNEL method distinguishes live cells from dead, it does not accurately determine whether the cells died by apoptosis or necrosis. False positives are often obtained when using the TUNEL method as a result of DNA fragments from cells that have died by necrosis: random DNA breakdown during necrosis generates DNA fragments that have 3'-OH ends. False negatives can also occur in certain cell types or situations where apoptosis does not lead to DNA laddering. Furthermore, the method is not quantitative since the amount of DNA fragments per cell is dependent upon the stage of apoptosis of the cell. In addition, this method is limited to use in flow cytometry and immunofluorescence, which renders it expensive and time consuming.

Another marker that is currently available is annexin, sold under the trademark APOPTEST™. This marker is used in the "Apoptosis Detection Kit" offered by R&D Systems. During apoptosis, a cell membrane's phospholipid asymmetry changes such that the phospholipids are exposed on the outer membrane. Annexins are a homologous group of proteins that bind phospholipids in the presence of calcium. A second reagent, propidium iodide (PI), is a DNA binding fluorochrome. When a cell population is exposed to both reagents, apoptotic cells stain positive for annexin and negative for PL, necrotic cells stain positive for both, live cells stain negative for both. This marker, however, suffers from a number of problems. Annexin has a strong potential for a lack of specificity due to the fact that it is not antigenic. As well, its use is limited to cells grown in suspension, however, most cells are adherent and are grown on a matrix.

The method also requires the use of live or unpreserved cells. Furthermore, this method requires the use of a flow cytometer, expensive equipment that is not always readily available.

There is therefore a great need for a specific, antigenic, versatile marker for the rapid detection of cell death by apoptosis, which can be used for research, diagnostics, and therapeutics. This marker must be able to distinguish between cell death by apoptosis and cell death by necrosis.

The classical cell model to study apoptosis is the isolated thymocyte, a small lymphocyte in the cortex of the thymus. This model, however, includes a number of limitations as follows: apoptosis occurs too rapidly, making it difficult to delineate the sequence of events, thymocytes are predisposed to apoptosis, and thymocytes are non-adherent, and the role of extracellular matrix proteins (ECM) in apoptosis cannot be studied. For these reasons, an adherent cell model was developed from which cells at four different stages of apoptosis can be isolated and studied (Desjardins and MacManus (1995) *Exp. Cell Res.* 216:380–387).

Recently, it was reported that human and rodent cells undergoing apoptosis express high levels of a protein, termed apoptosis specific protein (ASP) (Grand et al., (1995) *Exp. Cell Res.* 218:439–451). Induction of apoptosis coincides with the expression of ASP. ASP is not detected or is detected in very low amounts in viable cells and cells dying passively by necrosis. It was concluded that ASP constitutes a powerful marker for the diagnosis and quantitation of apoptosis.

The protein GP46 is known in the literature as HSP47, HSP46, or colligin. This protein was first discovered by Kurkinen et al., (1984) *J. Biol. Chem.* 259:5915–5922, who described a 47 kDa glycoprotein from murine parietal endoderm cells that bound specifically to gelatin, collagen I, and collagen IV, hence, the name colligin. Later, similar glycoproteins were described in other cell types, including L6 rat myoblasts, 3T3 fibroblasts, keratinocytes, and chick embryo fibroblasts (Cates et al., (1984) *J. Biol. Chem* 259:2646–2650; Taylor et al., (1985) *Exp. Cell Res.* 159:47–54; Hughes et al. (1987) *Eur. J. Biochem.* 163:57–65; and Nagata et al., (1986) *J. Cell. Biol.* 103:223–229). The similarity between these proteins was later confirmed by comparing cDNA sequences between some of the cell lines (Clarke and Sanwal (1992) *Biochim. Biophys. Acta* 1129:246–248).

GP46 is localized in the lumen of the endoplasmic reticuhim (ER) of the cell (Nandan et al., (1988) *Exp. Cell Res.* 179:289–297; Saga et al., (1987) *J. Cell Biol.* 105:517–527). It has an RDEL (Arg-Asp-Glu-Leu) sequence at the C-terminus which serves as an ER retention signal (Pelham, (1990) *Trends Biochem. Sci.* 15:483–486). GP46 is known to bind to denatured collagen, collagen I, collagen IV, and procollagen I. Its role may be to act as a molecular chaperone by assisting in protein folding of collagen during its synthesis (Jain et al. (1994) *Biochem. J.* 304:61–68; Nakai et al., (1992) *J. Cell Biol.* 117:903–914). It is a member of the serine-proteinase inhibitor family (serpin) and may protect procollagen I chains from degradation by inhibiting collagenase in the ER (Jain et al., (1994) *Biochem. J.* 304:61–68; Clarke et al., (1993) *J. Cell Biol.* 121:193–199).

A number of findings have linked the GP46 protein to apoptosis. It has been observed that GP46 mRNA increases in neuronal cells during apoptosis, and that the GP46 levels remain high for 48 hours (Higashi et al., (1994) *Brain Res.* 650:239–248). As well, it has been reported that when anti-sense RNA of GP46 is added to cells, apoptosis is induced and the cells die (Nagata et al., (1995) "Regulation and Function of Collagen-Specific Molecular Chaperone-Like Protein HSP47" in *J. Cell. Biochem. Suppl.* 190:195 and oral presentation at the Keystone Symposia on Sress Proteins in March, 1995).

This background information is provided for the purpose of making known information believed by the applicant to be of possible relevance to the present invention. No admission is necessarily intended, nor should be construed, that any of the preceding information constitutes prior art against the present invention. Moreover, publications referred to in the following discussion are hereby incorporated by reference in their entireties in this application.

SUMMARY OF THE INVENTION

It is therefore an object of the present invention to provide an accurate and specific method of detecting apoptosis, which is easier to perform, less expensive, and more suitable for widespread clinical and research use than existing methods. It is also an object of the present invention to provide a new method of monitoring and evaluating the efficacies of medical treatments for diseases involving apoptosis. It is a further object of the present invention to provide a new method for treating diseases involving apoptosis.

To achieve the foregoing and other objects, the invention provides anti-GP46 antibodies and fragments thereof to be used as markers of apoptosis in vitro and in vivo, as moieties for targeting apoptotic cells, and as therapeutic agents for the treatment of diseases involving apoptosis.

In summary, the present invention relates to antibodies and fragments thereof capable of specifically reacting with an antigenic determinant of GP46. These antibodies and fragments may be labeled with radionuclides, enzymes, enzyme substrates, enzyme cofactors, enzyme inhibitors, ligands (particularly haptens), fluorescers, chromophores, luminescers, or magnetic particles. These antibodies and fragments may be derived from vertebrates or invertebrates. These antibodies and fragments may be monoclonal or polyclonal.

In a preferred embodiment, the present invention relates to a human anti-GP46 antibody.

In another preferred embodiment, the present invention relates to a human anti-GP46 Fv antibody fragment.

The present invention also relates to an immortal cell line that produces anti-GP46 antibodies.

In a preferred embodiment, the present invention relates to an immortal cell line that produces human anti-GP46 monoclonal antibodies.

The present invention also relates to a diagnostic reagent for detection of apoptosis, comprising anti-GP46 antibodies or fragments thereof.

The present invention also relates to a method for the detection of apoptosis in a sample, which comprises contacting a sample to be tested for the presence of apoptosis with anti-GP46 antibodies or fragments thereof, thereby forming an immune complex, followed by determining the presence of the immune complex. The presence of the immune complex serves as a measure of apoptosis in the sample.

In one embodiment of the present invention, the method for the detection of apoptosis is used for research into apoptosis and for research relating to diseases in which apoptosis is involved. This method could also be used to diagnose the extent of damage caused by a particular disease or to evaluate the efficacy of drug treatments.

In one embodiment of the present invention, the method for the detection of apoptosis is used to monitor the treatment of a disease.

In a preferred embodiment, the method for the detection of apoptosis is used to monitor the treatment of cancer.

The present invention also relates to a method for the detection of sites of apoptosis in a patient, which comprises preparing a medically-useful antibody conjugate comprising an anti-GP46 antibody or fragment thereof and a medically-useful label; administering a safe and effective amount of the medically-useful antibody conjugate to the patient; and detecting the presence of GP46-antibody conjugate complexes in the patient.

In one embodiment of the present invention, the detection method for use in a patient detects sites of apoptosis caused by a particular disease, such as cancer, heart disease, neurodegenerative disorders, autoimmune disorders, and viral and bacterial infections.

In a preferred embodiment of the detection method for use in a patient, the medically-useful antibody conjugate is comprised of a human anti-GP46 Fv fragment labeled with a radionuclide, and the presence of GP46-antibody conjugate complexes in the patient are detected by radioactive imaging techniques such as gamma scintigraphy, emission computed tomography, and single photon emission computed tomography.

The present invention further relates to an antibody-drug conjugate comprising an anti-GP46 antibody or fragment thereof and a therapeutic agent.

The present invention also relates to a method of immunotherapy of a patient, comprising preparing an antibody-drug conjugate comprising an anti-GP46 antibody or fragment thereof and a therapeutic agent, and administering an effective amount of the medically-useful antibody conjugate to the patient.

In one embodiment of this method of immunotherapy, the therapeutic agent is delivered to apoptotic cells for the prevention or treatment of a disease involving apoptosis, such as cancer, heart disease, neurodegenerative disorders, autoimmune disorders, and viral and bacterial infection. The therapeutic agent may be a radionuclide, a drug, a toxin, a biological response modifier, or a second antibody.

The present invention further relates to a pharmaceutical composition for use in the prophylactic or therapeutic treatment of diseases involving apoptosis, said composition comprising an anti-GP46 antibody or fragment thereof and a pharmaceutically acceptable carrier.

The present invention further relates to a method of treating a patient, said method comprising administering a prophylactically or therapeutically effective amount of an anti-GP46 antibody or fragment thereof and a pharmaceutically acceptable carrier.

In a preferred embodiment of this method of treating a patient, a human patient is treated to avoid, reduce, or eliminate the effects of diseases involving apoptosis.

The present invention also relates to a diagnostic kit for the detection of apoptosis, comprising a container containing at least one anti-GP46 antibody or fragment thereof. This anti-GP46 antibody or fragment thereof may be attached to a solid carrier.

BRIEF DESCRIPTION OF THE DRAWINGS

While the specification concludes with claims particularly pointing out and distinctly claiming the subject matter regarded as forming the present invention, it is believed that the invention will be better understood from the following preferred embodiments of the invention taken in connection with the accompanying drawings in which:

DETAILED DESCRIPTION OF THE INVENTION

Figure 1A:
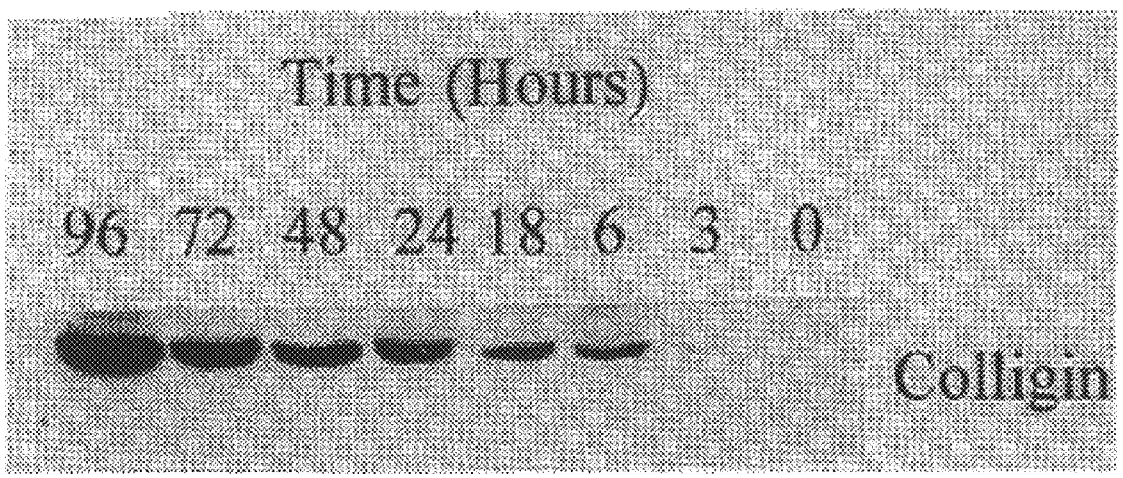
FIG. 1 demonstrates the increase in GP46 in HT29 cells wherein apoptosis was induced by treatment with 5 $\mu$M VM26 for 24 h. Changes in the amount of GP46 were determined over 96 h by Western Blotting. Time 0 is when VM26 was added. Panel A shows the autoradiograph. In Panel B, the results are presented in a graph.

Unless defined otherwise all technical and scientific terms used herein have the same meaning as commonly understood by one of ordinary skill in the art to which this invention belongs.

The following common abbreviations are used throughout the specification and in the claims:

The term "anti-GP46 antibodies" means any antibodies or fractions thereof that have been produced using the GP46 protein as an immunogen. The term includes recombinant, chimeric, and affinity modified forms made by techniques of molecular biology well known in the art.

The term "Fab" means a antigen binding fragment which is obtained by cleaving an antibody with papain in the hinge region yielding two Fab fragments, each having the heavy and light chain domains of an antibody, plus an Fc portion.

The term "Fc" means the antibody fragment which may activate complement.

The term "Fv fragments" means heterodimers of the heavy and light chain variable domains of an antibody. These variable domains may be joined by a peptide linker or by an engineered disulphide bond.

The abbreviation, GP46, is a protein that is also known in the literature as HSP46, HSP47, colligin, collagen-binding protein, collagen chaperone, 46 kD, or 47 kD.

The abbreviation, PI is propidium iodide.

The term "recombinant antibodies or fragments" collectively includes chimeric or recombinant forms of the anti-GP46 antibodies or fragments thereof wherein the Fc domain is substituted for an Fc domain of another species or isotype, affinity modified forms of the anti-GP46 antibodies or fragments thereof wherein the binding sites are altered, avidity modified forms of the anti-GP46 antibodies or fragments thereof wherein the hinge regions are altered, immunoreactive fragments thereof, and combinations thereof.

The present invention resides in the discovery that levels of GP46 protein increase significantly upon induction of apoptosis. At the onset of apoptosis, GP46 increases many fold in dying cells to reach a maximum concentration at the end of the apoptotic cell death process. Significant levels of GP46 remain even in dead apoptic cells. The GP46 protein, however, does not increase in concentration during necrotic cell death. The presence of GP46 can therefore serve as a marker for the early detection of apoptosis.

In the present invention, anti-GP46 antibodies or fragments thereof are used to detect apoptosis with applications in research, diagnostics, and disease treatment. As well, these antibodies and fragments are used as targeting moieties to deliver compounds to apoptotic cells. Furthermore, the anti-GP46 antibodies or fragments thereof can be used in therapeutic applications to treat diseases involving apoptosis.

Generation of Antibodies

The antibodies of the present invention, or fragments thereof, can be:
  a) naturally occuring;
  b) produced by recombinant DNA technology;
  c) produced by biochemical or enzymatic fragmentation of larger molecules;
  d) produced by methods resulting from a combination of a) to d); or
  e) produced by any other means for producing antibodies.

The anti-GP46 antibodies of the present invention can be monoclonal or polyclonal, although monoclonal antibodies are preferred. In general, antibodies may be obtained by injecting the desired immunogen into a wide variety of vertebrates or invertebrates in accordance with conventional techniques. While rodents, particularly mice, are preferred, other species may be employed, such as Lagomorpha, or members of the bovine, ovine, equine, porcine, or avian families. Immunization of these animals can be readily performed and their lymphocytes, particularly splenocytes, may be obtained for fusions.

Immunization protocols are well known and can vary considerably yet remain effective (Goding, *Monoclonal Antibodies: Principles and Practice* (2nd ed.) (Academic Press, 1986). Isolated proteins, synthetic peptides, and bacterial fusion proteins which contain antigenic fragments of the GP46 molecule may be used as immungens. Preferably the immunogen of peptides or recombinant proteins will be enriched for proteins or fragments thereof containing the epitopes to which antibody-producing B cells or splenocytes are desired. More particularly, solutions containing disrupted virus lysates or extracts, or supernatants of biolocically-expressed recombinant proteins or disrupted expression vectors, may be enriched for glycoproteins, as desired, using purification methods, such as, for example, polyacrylamide gel electrophoresis. Lectin affinity purification is a preferred and convenient method for purification of GP46, e.g., affinity purifcation using concanavilin A (ConA) lectin or affinity purification using anti-GP46 antibodies. The extent to which GP46 are purified from the solutions for use as an immunogen can vary widely, i.e., from less than 50%, usually or at least 75% to 95%, desirably 95% to 99% and, most desirably, to absolute homogeneity.

Once the proteins or peptides thereof have been purified to the extent desired, they may be suspended or diluted in an appropriate physiological carrier for immunization, or may be coupled to an adjuvant. Immunogenic amounts of antigenic preparations enriched in GP46 proteins, or antigenic portions thereof, are injected, generally at concentrations in the range of 1 ug to 100 mg/kg of host. Administration may be by injection, such as intramuscularly, peritoneally, subcutaneously, or intravenously. Administration may be one or a plurality of times, usually at one to four week intervals.

Immunized animals are monitored for production of antibody to the desired antigens, then the spleens are removed and splenic B-lymphocytes isolated and fused with a myeloma cell line or transformed. The transformation or fusion can be carried out in conventional ways, the fusion technique being described in an extensive number of patents, such as U.S. Pat. Nos. 4,172,124; 4,350,683; 4,363,799; 4,381,292; and 4,423,147. The manner of immortalization is not critical, but the most common method is fusion with a myeloma fusion partner. Other techniques of immortalization include EBV transformation, transformation with bare DNA, such as oncogenes or retroviruses, or any other method that provides for stable maintenance of the cell line and production of monoclonal antibodies. The general process for obtaining monoclonal antibodies has been described (Kohler and Milstein (1975) *Nature* 256:495–497). Human monoclonal antibodies may be obtained by fusion of the spleen cells with an appropriate human fusion partner, such as WI-L2, described in European Application No. 82.301103.6. A detailed technique for producing mouse X-mouse monoclonal antibodies has been taught (Oi and Herzenberg (1980) in Mishell and Shiigi (eds.) *Selected Methods in Cellular Immunology* 351–372). The resulting hybridomas are screened to isolate individual clones, each of which secretes a single antibody species to the antigen.

The immortalized cell lines may be cloned and screened in accordance with conventional techniques, and antibodies in the cell supernatants detected that are capable of binding to GP46. The appropriate immortalized cell lines may then be grown in vitro or injected into the peritoneal cavity of an appropriate host for production of ascites fluid. Immortalized hybridoma cell lines can be readily produced from a variety of sources. Alternatively, these cell lines may be fused with other neoplastic B-cells, where such other B-cells may serve as recipients for genomic DNA coding for the antibody.

The monoclonal antibody secreted by the transformed or hybrid cell lines may be of any of the classes or subclasses of immunoglobulins, such as IgM, IgD, IgA, $IgG_{1-4}$, or IgF. As IgG is the most common isotype utilized in diagnostic assays, it is often preferred.

To circumvent the possible antigenicity in a human host of a monoclonal antibody derived from an animal other than human, chimeric antibodies may be constructed. For example, the antigen binding fragment of an immunoglobulin molecule (variable region) may be connected by peptide linkage to at least part of another protein not recognized as foreign by humans, such as the constant portion of a human immunoglobulin molecule. This can be accomplished by fusing the animal variable region exons with human kappa or gamma constant region exons. Various techniques are known to the skilled artisan, such as those described in PCT 86/01533, EP171496, and EP173494.

Antibody Engineering

The anti-GP46 antibodies may be used intact, or as fragments, such as Fv, Fab, and $F(ab')_2$ Such antibody fragments provide better diffusion characteristics in vivo than the whole anti-GP46 antibody, due to their smaller size. The means for engineering antibodies by recombinant DNA and chemical modification methods are considered well-known in the art.

The anti-GP46 antibodies are fragmented to obtain highly immunoreactive $F(ab')_2$, F(ab'), and Fab fragments using the enzyme pepsin by methods well known in the art (see Colcher et al., (1983) *Cancer Res.* 43:736–742).

Anti-GP46 antibodies or fragments thereof are also made into recombinant forms by techniques of molecular biology well known in the art (see Rice et al., (1982) *Proc. Natl. Acad. Sci. USA* 79:7862–7865; Kurokawa et al. (1983) *Nucleic Acids Res.* 11:3077–3085; Oi et al., (1983) *Proc. Natl. Acad. Sci. USA* 80:825–829; Boss et al., (1984) *Nucleic Acids Res.* 12:3791–3806; Boulianne et al., (1984) *Nature (London)* 312:643–646; Cabily et al., (1984) *Proc. Natl. Acad. Sci. USA* 81:3272–3277; Kenten et al., (1984) *Proc. Natl. Acad. Sci. USA* 81:2955–2959; Liu et al., (1984) *Proc. Natl. Acad. Sci. USA* 81:5369–5373; Morrison et al., (1984) *Proc. Natl. Acad. Sci. USA* 81:6851–6855; Neuberger et al., (1984) Nature (London) 312:604–608; Potter et al., (1984) *Proc. Natl. Acad. Sci. USA* 81:7161–7165; Neuberger et al., (1985) *Nature (London)* 314:268–270; Jones et al., (1986) *Nature (London)* 321:522–525; Oi et al., (1986) *BioTechniques* 4:214–221; Sahagan et al., (1986) *J. Immunol.* 137:1066–1074; Sun et al., (1986) *Hybridoma S* (Supp. 1):S17–S20; and Sun et al., (1987) *Proc. Natl. Acad. Sci. USA* 84:214–218).

More specifically, the antibodies and fragments thereof may be altered to a chimeric form by substituting antibody fragments of another species, e.g., human constant regions (Fc domains) for mouse constant regions by recombinant DNA techniques known in the art as described in the above cited references. These Fc domains can be of various human isotypes, i.e., $IgG_1$, $IgG_2$, $IgG_3$, $IgG_4$, or IgM.

In addition, the antibodies and fragments thereof may be altered to an affinity modified form, avidity modified form, or both, by altering binding sites or altering the hinge region using recombinant DNA techniques well known in the art as described in the above cited references.

The recombinant antibody forms may also be fragmented to produce immunoreactive fragments $F(ab')_2$, F(ab'), and Fab in the same manner as described.

The preferred antibody fragments are Fv fragments. Fv fragments are the smallest functional modules of antibodies required to maintain the binding and specificity of the whole antibody. They are heterodimers composed of a variable heavy chain and a variable light chain domain. Proteolytic digestion of antibodies can yield isolated Fv fragments, but the preferred method of obtaining Fvs is by recombinant technology (See Skerra and Pluckthun (1988) *Science* 240:1038–1041).

Fvs can be noncovalently-associated $V_H$ and $V_L$ domains, although these tend to dissociate from one another. Stable Fvs can be produced by making recombinant molecules in which the $V_H$ and $V_L$ domains are connected by a peptide linker so that the antigen-combining site is regenerated in a single protein. These recombinant molecules are termed single chain Fvs (scFvs). The means for preparing scFvs are known in the art (See: Raag and Whitlow (1995) *FASEB* 9:73; Bird et al., (1988) *Science* 242:423–426; Huston et al., (1988) *Proc. Natl. Acad. Sci. USA* 85:5879–5883). Alternatively, the two variable domains can be joined and stabilized by an engineered disulphide bond; these are termed disulfide Fvs (dsFvs) (Reiter and Pastan (1996) *Clin. Cancer Res.* 2:245–252).

Labeling of Antibodies or Fragments

The anti-GP46 antibodies of this invention, or fragments thereof, may be used without modification or may be modified in a variety of ways, for example, by labeling. Labeling is intended to mean joining, either covalently or non-covalently, a label which directly or indirectly provides for a means of detection. A label can comprise any material possessing a detectable chemical or physical property. A wide variety of labels are known, including radionuclides, enzymes, enzyme substrates, enzyme cofactors, enzyme inhibitors, ligands (particularly haptens), fluorescers, chromophores, luminescers, and magnetic particles. These labels are detectable on the basis of either their own physical properties (eg., fluorescers, chromophores and radioisotopes), or their reactive or binding properties (eg., enzymes, substrates, cofactors and inhibitors). These materials are well known to one skilled in the art.

Antibody Conjugates

In addition, the antibodies of the present invention or fragments thereof can be used as target-specific carrier molecules. An antibody may be bound to a toxin to form an immunotoxin, to a radioactive material to form a radiopharmaceutical, or to a drug to form a pharmaceutical, such as fusion proteins. Methods for producing immunotoxins, radiopharmaceuticals, and fusion proteins are well known (See: Reiter and Pastan (1996) *Clin. Cancer Res.* 2:245–252; (1984) *Cancer Treatment Reports* 68:317).

Detection of Apoptosis

Anti-GP46 antibodies or fragments thereof can be used to detect apoptosis in various biological samples by combining them with the sample in question. Biological samples can include, but are not limited to, in vitro tissue biopsy samples (brain, skin, lymph nodes, spleen, breast, liver, prostate, colon, etc.), in vivo tissues (spleen, colon, skin, pancrese, liver, breast, prostate, etc.), and cell cultures. Presence of apoptosis is tested for by incubating the anti-GP46 antibody with the biological sample under conditions conductive to GP46 immune complex formation, followed by the detection of complex formation.

The antibodies or fragments of the present invention can be either labeled or unlabeled for this purpose. Typically, diagnostic assays entail the detection of the formation of a complex through the binding of the monoclonal antibody to GP46. When unlabeled, the antibodies find use, for example, in agglutination assays. In addition, unlabeled antibodies can be used in combination with other labeled antibodies (second antibodies) that are reactive with the monoclonal antibody, such as antibodies specific for immunoglobulin. Alternatively, the antibodies can be directly labeled.

GP46 immune complexes can be detected using any procedure known in the art. Numerous types of immunoassays are available, including enzyme immune assay (EIA), enzyme multiplied immunoassay technique (EMIT), enzyme-linked immunosorbend assay (ELISA), radioimmune assay (RIA), fluorescence immune assay, either single or double antibody techniques, and other techniques where either the peptides or antibodies of this invention are labeled with some detectable tag. (See Maggio *Enzyme Immunoassay* (CRC Press, 1981); U.S. Pat. Nos. 3,817,827; 3,850,752; 3,901,654; 3,935,074; 3,984,533; 3,996,345; 4,034,074; and 4,098,876).

One procedure for detection of the GP46 immune complexes is the Enzyme Linked Immunosorbent Assay (ELISA). In a classical model of ELISA, specific antibody is coated on a solid phase. This antibody is typically referred to as the 'capture antibody'. Traditional solid support used for the solid phase has been predominantly polystyrene surfaces such as microtiter plates or test tubes, polyethylene or polycarbonate and nylon, and nitrocellulose membranes, more recently, a hydrophobic synthetic polyester cloth sheet has been utilized as the solid phase. A test sample containing an antigen complimentary to the specific antibody is added to the solid phase allowing the antigen to be specifically captured by the antibody immobilized on the solid phase.

Any non-specific substances in the sample are then removed by simple washing with buffer solutions. Subsequently, an antibody-enzyme conjugate is added which binds to the antigen, or some part of the GP46 immune complex. After washing away the excess unbound conjugates, an appropriate substrate solution is added so that a detectable product, such as a colored product, is generated and in amounts directly proportional to the GP46 antigen present in the test sample. This procedure is well established and well known to those skilled in the art.

In one embodiment, GP46 immune complex formation is detected through use of a second antibody capable of binding to the anti-GP46 monoclonal antibody. In another embodiment, an anti-GP46 monoclonal antibody is attached to a solid phase support which is then contacted with a biological sample. Following an incubation step, labeled monoclonal antibody is added to detect the bound antigen.

Anti-GP46 antibodies or fragments thereof may be coupled to a solid-phase to remove GP46 from a human or animal sample. One procedure involves applying a known amount of Type 1 collagen to a collagen-binding solid support, washing a GP46 protein extract across said collagen-solid support, washing away excess material, applying anti-GP46 antibody, washing away excess antibody, and detection of GP46-antibody complex by standard commercially available anti-antibody detection system known to those skilled in the art. This procedure can be both qualitative and quantitative.

In another procedure, the antibodies can be attached to particulate carrier materials to form water-insoluble immunological reagents by physical or chemical means, including adsorption or covalent reaction with reactive groups on the surface of the materials. Many useful reactive groups are known in the art for antibody attachment, which groups can be part of the chemical structure of the carrier materials, or can be added by coating or chemical treatment of an inert material. One skilled in the art would readily understand how to prepare such materials to have any of the following reactive groups: carbosy, 2-substituted ethylsulfonyl, vinylsulfonyl, epoxy, aldehyde, active halo atoms, amino, hydrazide, and active esters such as succimimidoxy carbonyl.

Procedures for attaching antibodies to particles having reactive groups are well known, as described for example in U.S. Pat. No. 3,925,157, U.S. Pat. No. 4,181,636, U.S. Pat. No. 4,703,018 and EP-A-0,323,692. In general, antibodies are mixed with the particles under suitable conditions depending upon the attachment form (adsorption, covalent, or use of a linking group). A worker skilled in the art would readily know what conditions should be used for each procedure. For example, for attachment to particles having reactive halo atoms, activated 2-substituted ethylsulfonyl or vinylsulfonyl groups, the antibodies are generally mixed with the particles for up to 24 hours at a temperature of from about 20° C. to about 40° C. in a suspension buffered at a pH of from about 7 to about 10. If carboxy groups are used for attachment, the well known carbodiimide activators can be used, as well as carbomoylonium compounds as described in EP-A-0,308,235. Antibodies can be absorbed on particles by incubating particles and antibodies in suspension at suitable temperature for several hours.

Kits can also be supplied for use with the subject antibodies in the detection of apoptosis or for the presence GP46. Thus, the anti-GP46 antibodies of the present invention or fragments thereof may be provided, usually in a lyophilized form, either alone or in conjunction with additional antibodies specific for different epitopes of GP46. The antibodies, which may be conjugated to a label or unconjugated, are included in the kits with buffers such as Tris, phosphate, or carbonate, stabilizers, biocides, inert proteins such as bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the monoclonal antibody is employed, this will usually be present in a separate vial. The second antibody is typically conjugated to a label and formulated in an analogous manner with the antibody formulations described above.

Distinguishing Apoptosis from Necrosis

The methods of the present invention can be combined with either the TUNEL method or with the use of propidium iodide (PI) in order to identify cells dying by apoptosis as opposed to cells dying by necrosis. The TUNEL method is used in fixed-dead cells. Cells in which an increase in GP46 (above control) is observed combined with either a positive TUNEL or a positive PI reading indicated apoptotic cells; cells in which no increase in GP46 levels is detected in combination with either a positive TUNEL or a positive PI reading indicates necrotic cell death.

Pharmaceutical Formulations and Use

The antibodies or fragments thereof of this invention can also be incorporated as components of pharmaceutical compositions. The composition should contain a therapeutic or prophylactic amount of at least one of the antibodies or fragments thereof of this invention with a pharmaceutically effective carrier. A pharmaceutical carrier should be any compatible, non-toxic substance suitable to deliver the antibodies or fragments thereof to the patient. Sterile water, alcohol, fats, waxes, and inert solids may be used as the carrier. Pharmaceutically acceptable adjuvants (buffering agents, dispersing agents) may also be incorporated into the pharmaceutical composition. Such composition can contain a single monoclonal antibody, alternatively, a pharmaceutical composition can contain one or more antibodies or fragments thereof to form a "cocktail."

The antibodies or fragments thereof of this invention are particularly useful for oral or parenteral administration. Preferably, the pharmaceutical compositions may be administered parenterally, i.e., subcutaneously, intramuscularly or intravenously. Thus, this invention provides compositions for parenteral administration which comprise a solution of the monoclonal antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, etc. The concentration of antibody in these formulations can vary widely, i.e., from less than about 0.5%, usually at or at least about 1% to as much as 15 or 20% by weight and will be selected primarily based on fluid volumes, viscosities, etc., preferably for the particular mode of administration selected. Thus, a typical pharmaceutical composition for intramuscular injection could be made up to contain 1 ml sterile buffered water, and 50 mg of monoclonal antibody. A typical composition for intravenous infusion could contain 250 ml of sterile Ringer's solution and 150 mg of monoclonal antibody. Actual methods for preparing parenterally administrable compositions will be known or apparent to those skilled in the art and are described in more detail in, for example, Remington's Pharmaceutical Science, 15th Ed., Mack Publishing Company, Easton, Pa. (1980), which is incorporated herein by reference.

For therapeutic and/or preventative use, the composition may be in solid or liquid form and presented in a conventional manner for parenteral or oral application. The compositions may be in the form of injectable solutions or in the form of tablets, capsules, solutions, or suspensions.

The antibodies or fragments thereof of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions or cocktails containing the present antibodies or fragments thereof can be administered for the prophylactic and/or therapeutic treatment. In therapeutic application, compositions are administered to a patient already diagnosed with a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. In prophylactic applications, compositions containing the present antibodies or a cocktail thereof are administered to a patient not already having a specific disease, but perhaps recently exposed to or thought to have been exposed to, or at risk of developing the disease, to enhance the patient's resistance to the disease. An amount is defined to be a "prophylactically effective dose." In this use, the precise amounts again depend upon the patient's state of health.

Single or multiple administrations of the compositions can be carried out with dose levels and pattern being selected by the treating physician. In any event, the pharmaceutical formulations should provide a sufficient quantity of the antibodies of this invention to effectively treat the patient.

In Vivo Diagnostic Assays

In vivo diagnostic assays of apoptosis using the anti-GP46 antibodies or fragments thereof are described in more detail below.

The anti-GP46 antibodies or fragments thereof are conjugated to an imaging marker and administered to a patient. Alternatively, an imaging marker or a linker conjugated marker can be administered after administration of the antibody or fragment. The presence of the imaging marker in the patient is detected by exposing the patient to an appropriate means for detecting the marker.

Administration and detection of the antibody- or fragment-imaging marker conjugate as well as methods of conjugation of the antibody or fragment to the imaging marker are accomplished by methods readily known to or readily determined by those skilled in the art. These are described, for example, in Goldenberg et al., (1978) *New England J. Med.* 298:1384–1388; Goldenberg et al., (1983) *JAMA* 250:630–635; Goldenberg et al., (1983) *Gastroenteral,* 84:524–532; Siccardi et al., (1986) *Cancer Res.* 46:4817–4822; Epenetos et al., (1985) *Cancer* 55:984–987; Philben et al., (1986) *Cancer* 57:571–576; Chiou et al., (1985) *Cancer Res.* 45:6140–6146; Hwang et al., (1986) *J. Natl. Cancer Inst.* 76:849–855; Colcher et al., (1983) *Cancer Res.* 43:736–742; Colcher et al., (1983) In *Laboratory Research Methods in Biology and Medicine Immunodiagnostics* (New York; Liss) 215–258; Keenan et al., (1984) *J. Nucl. Med.* 25:1197–1203; Colcher et al., (1987) *Cancer Res.* 47:1185–1189; Esteban et al., (1987) *Intl. J. Cancer* 39:50 . 59; Martin et al., (1984) *Curr. Surg.* 41:193–194; Martin et al., (1986) *Hybridoma* 5:S97–S108; and Martin et al., (1985) *Am. J. Surg.* 150:672–675.

Examples of imaging markers which can be conjugated to the antibody or fragment are well known to those skilled in the art and include substances that can be detected by diagnostic imaging using a gamma scanner or hand held gamma probe or Positron Emission Tomography or the like, as described in the references cited above, and substances that can be detected by nuclear magnetic resonance imaging using a nuclear magnetic resonance spectrometer or the like as described in the references cited above.

Suitable examples of substances which can be detected using a gamma scanner or the like include $^{125}I$, $^{131}I$, $^{123}I$, $^{111}In$, and $^{99m}Tc$. $^{111}In$ and $^{99m}Tc$ are preferred due to their low energy and suitability for long range detection.

An example of a substance which can be detected using a nuclear magnetic resonance spectrometer or the like is the nuclear magnetic spin-resonance isotope gadolinium (Gd).

In Vivo Treatment

A pharmaceutically effective amount of an anti-GP46 antibody or fragment thereof conjugated or conjugated to a therapeutic agent is administered to a patient.

Methods of preparing and administering the antibody- or fragment-therapeutic agent conjugates as well as suitable dosages will depend on the age and weight of the patient and the therapeutic agent employed and are well known to or readily determined by those skilled in the art. Representative protocols are described in the references cited below.

Examples of the antibody- or fragment-therapeutic agent conjugates which can be used in therapy include antibodies coupled to radionuclides such as $^{131}I$, $^{90}Y$, $^{105}Rh$, $^{47}Sc$, $^{67}Cu$, $^{212}Bi$, and $^{211}At$ (described in Goldenberg et al., (1981) *Cancer Res.* 41:4354–4360; Carrasquillo et al., (1984) *Cancer Treat. Rep.* 68:317–328; Zalcberg et al., (1984) *J. Nat. Cancer Inst.* 72:697–704; Jones et al., (1985) *Int. J. Cancer* 35:715–720; Lange et al., (1985) *Surgery* 98:143–150; Kaltovich et al., (1986) *J. Nucl. Med.* 27:897; Order et al., (1982) *Int. J. Radiother. Oncol. Biol. Phys.* 8:259–261; Courenay-Luck et al., (1984) *Lancet* 1:1441–1443; and Ettinger et al., (1982) *Cancer Treat. Rep.* 66:289–297); antibodies coupled to drugs or biological response modifiers such as methotrexate, adriamycin, and interferon (described in Chabner et al., (1985) *Cancer, Principles and Practice of Oncology,* Vol. 1 (Philadelphia, J. B. Lippincott) 290–328; Oldham et al., (1985) *Cancer, Principles and Practice of Oncology,* Vol. 2 (Philadelphia; J. B. Lippincott) 2223–2245; Deguchi et al., (1986) *Cancer Res.* 46:3751–3755; Deguchi et al., (1985) *Fed. Proc.* 44:1684; Embleton et al., (1984) *Br. J. Cancer* 49:559–565; and Pimm et al., (1982) *Cancer Immunol. Immunother.* 12:125–134); antibodies coupled to toxins (described in Uhr et al., (1983) *Monoclonal Antibodies and Cancer* (Academic Press) 85–98; Vitetta et al., (1984) in Abelson (ed.) *Biotechnology and Bio. Frontiers* 73–85; and Vitetta et al., (1983) *Science* 219:644–650); heterobifunctional antibodies such as antibodies coupled or combined with another antibody so that the complex binds both to the carcinoma and effector cells, e.g., killer cells such as T cells (described in Perez et al., (1986) *J. Exper. Med.* 163:166–178; and Lau et al., (1985) *Proc. Natl. Acad. Sci. USA* 82:8648–8652); and native, i.e., non-conjugated or non-complexed, antibody (described in Herlyn et al., (1982) *Proc. Natl. Acad. Sci. USA* 79:4761–4765; Schulz et al., (1983) *Proc. Natl. Acad. Sci. USA* 80:5407–5411; Capone et al., (1983) *Proc. Natl. Acad. Sci. USA* 80:Z328–7332; Sears et al., (1985) *Cancer Res.* 45:5910–5913; Neopom et al., (1984) *Proc. Natl. Acad. Sci. USA* 81:2864–2867; Koprowski et al., (1984) *Proc. Natl. Acad. Sci. USA* 81:216–219; and Houghton et al., (1985) *Proc. Natl. Acad. Sci. USA* 82:1242–1246).

In this method, the antibody- or fragment-therapeutic agent conjugate can be delivered to the site of apoptosis thereby directly exposing the apoptotic cells to the therapeutic agent.

Uses

The physiological and pathological implications of apoptosis render applications of anti-GP46 Mab and fragments thereof far reaching, including use in research, diagnostics, and therapy.

Uses in Research

The present invention comprises a specific marker for apoptosis, which discriminates between cells dying by apoptosis and those dying by necrosis. This marker could be used by scientists who are working on determining mechanisms of apoptosis. This marker could be used with whole animal models, with cells, or with tissue slices.

These markers of apoptosis could also be used in research relating to diseases in which apoptosis is involved, both to determine the mechanisms of the diseases and method of treatment. For example, anti-GP46 antibodies could be used in cancer research, where a potential chemotherapeutic drug could be tested for its ability to induce apoptosis. This could be done by exposing a cell sample to different concentrations of the test drug. The cells would then be analyzed for the presence of GP46 using the anti-GP46 antibodies or fragments thereof of the present invention. The ability of the chemotherapeutic test drug to induce apoptosis could be determined and compared to the apoptosis induction of well known drugs.

Additionally, anti-GP46 antibodies or fragments thereof could be used as markers to assess the dose response of cells to chemotherapeutic drugs in order to determine ideal dosages for treatment. A desirable dose would be one that induces apoptosis, but not necrosis in tumour cells.

The present invention could also be used in the basic research of and drug development for neurodegenerative disorders such as Alzheimer's disease, Parkinson's disease, and ALS, including neuronal post-ischemic damage in stroke. For example, cells could be treated with an apoptosis inhibitor test drug at different concentrations and at different times post-apoptosis induction. Cells would then be collected at chosen times after the introduction of the test drug. The anti-GP46 antibodies and fragments thereof would provide a method of assessing the drug's apoptosis inhibitory potency. It would also allow determination of the stage of apoptosis at which the test drug has an inhibitory effect and the stage at which the drug is not longer effective.

As a further use in research of the present invention, companies that produce monoclonal antibodies require a reliable antigenic marker of apoptosis to indicate when the hybridomas are at peak antibody production. This occurs right before cells die by apoptosis. Anti-GP46 antibodies and fragments thereof may be excellent monitoring tools for optimizing peak harvest time.

Use in Diagnostic Assays

The method of the present invention could also be used to diagnose the extend of damage caused by a particular disease. For example, there is an enormous use for anti-GP46 antibodies as a diagnostic marker for post-ischemia neuronal damage by apoptosis. The TUNEL method has proven to be an inadequate marker for estimation of neuronal damage by necrosis versus apoptosis within in vivo and in vitro models. With anti-GP46 antibodies, however, it would be possible not only to quantify the severity of the damage caused by ischemia but also the proportion of cell death that was caused by apoptosis at various time points. This knowledge is important for designing and monitoring apoptosis inhibitor drug therapies, especially in terms of effectiveness, doses, and treatment schedule of the drugs. The same strategy could also be applied to neurodegenerative diseases.

The anti-GP46 antibodies or fragments thereof can also be used in nuclear medical imaging. In this procedure, a radionuclide, which has an affinity for a particular body part such as the brain, thyroid gland, or bone marrow, is administered to a patient. Radiation is then emitted from the body part of interest, and is detected by a scintillation camera device which forms an image of the body part based on the concentration and distribution of the radioactive isotope within the body part. More recently, the scintillation camera systems have been used to obtain tomographic images in studies known as emission computed tomography (ECT) or single photon emission computed tomography (SPECT). Iodinated scFvs are ideal for diagnostic imaging of specific tissues because of their rapid clearance from the body.

Use in Treatment

The method of the present invention could be used to evaluate whether a specific drug treatment is inducing or inhibiting apoptosis in a patient. For example, the present invention could be used in medical cancer diagnostics. A biopsy would be performed on the patient before treatment and then again approximately seven days after the treatment was initiated. An increase in GP46 protein in the seven-day sample relative to the pre-treatment sample would indicate that apoptosis had been induced in the tumour by the chemotherapeutic drug. This would allow clinicians to do an early assessment of a chemotherapy and gauge the performance of a treatment in a patient in timely manner. It would allow oncologists to make adjustments to the treatment if the results are negative, rather than putting the patient through a full cycle of inefficient treatment.

Anti-GP46 antibodies and fragments thereof are of particular value in clinical applications. As seen in Nagata et al., (1995) "Regulation and Function of Collagen-Specific Molecular Chaperone-Like Protein, HSP47" in *J. Cell. Biochem.* Suppl. 190:195, when the production of GP46 is inhibited by anti-sense RNA, apoptosis is induced. Anti-GP46 antibodies and fragments thereof may have a role in the treatment of patients by either inducing or inhibiting apoptosis in certain cells. This could have therapeutic applications in such diseases as cancer, heart disease, neurodegenerative disorders, autoimmune disorders, and viral infections.

Anti-GP46 antibodies and fragments thereof can also be used as targeting moieties to be used in the therapy of human diseases. By conjugating an effector to an anti-GP46 antibody or fragment, the antibody or fragment could be used to deliver promising therapeutic agents to apoptotic cells. A large number of effectors could be fused to scFvs to make a variety of therapeutic agents. For example, a truncated toxin could be fused to a recombinant anti-GP46 Fv to produce an immunotoxin. Targeting of these proteins to particular apoptotic cells would avoid toxicity to normal tissues.

Advantages

The use of anti-GP46 antibodies or fragments thereof to detect apoptosis has numerous advantages over other methods currently on the market. Firstly, the use of anti-GP46 antibodies or fragments thereof can distinguish cells that are dead or dying by apoptosis from those that are dead by necrosis; thus, the present invention provides reliable results; necrotic cells do not test positive. In contrast, most cell death kits currently on the market cannot distinguish cells that are dying by apoptosis from those dying by necrosis. The current products can only determine whether cells are dead or alive, thus, they produce false positives, which result in unreliable data.

In addition, the present invention, as opposed to cell death kits currently available, is versatile, enabling the detection of apoptosis in most cell types. It can be used with both tissue samples and cell lines.

Another advantage of the present invention is that apoptotic cells can be identified at an early stage of apoptosis. This is in contrast to current cell death kits that identify the 180-bp DNA ladder, an end-point in the apoptotic pathway.

Some of the protocols used by current products are time consuming and require sophisticated laboratory equipment and expertise. A further advantage of the present invention is that it can be used with a choice of qualitative and quantitative protocols adaptable to various laboratory equipment and expertise. For example, the present invention can be applied using common laboratory techniques such as ELISA and immunochemistry where no specialized laboratory equipment is required. It can also be applied using specialized equipment such as a flow cytometer. Depending upon the technique used, the present invention can achieve time savings of up to 60 percent.

There are no medical diagnostic products currently on the market that provide an early measure of apoptosis in relation to a chemotherapeutic treatment. The present invention can furnish this. It can be used to evaluate whether a specific drug treatment is inducing or inhibiting apoptosis in a patient. This could provide crucial treatment assessment weeks before traditional methods and at a fraction of the cost.

While the present invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The present invention will be illustrated by, but is not intended to be limited to, the following example.

EXAMPLE 1

Demonstration that Levels of GP46 Increase During Apoptosis

This method of detecting cell death by apoptosis can be demonstrated in an adherent cell line. Levels of GP46 present in apoptotic cells were detected by using specific labeled anti-GP46 monoclonal antibodies.

Materials:

Teniposide (VM26) was obtained from Bristol-Myers Squibb Laboratories (Montreal, PQ, Canada) as a sterile 15.23 mM solution in ethanol and stored at 4° C. $I^{125}$-rabbit anti-mouse IgG was purchased from New England Nuclear. Rabbit anti-mouse IgG conjugated with rhodamine was purchased from Cedarlane Laboratories. Hybridomas were a gift from Dr. B. D. Sanwal. (University of Western Ontario, London, ON, Canada).

Cell Culture:

HT29 cells (Fogh and Trempe "Human Tumor Cells" in Fogh (ed.) *In Vitro* (New York:: Plenum, 1975) 115–159) were maintained in Delbecco's modified Eagle's medium (DME) (GIBCO BRL Life Technologies, Inc.) supplemented with 10% fetal calf serum, 40 µg/ml gentamycin, and 25 mM glucose. Cells were subcultured every seven days and only those cells between passage numbers 140 and 150 were used.

Treatment of HT29 cells with VM26:

Experiments were carried out by subculturing HT29 at a density of $2.5 \times 10^6$ cells in 10 ml DME per 100-mm plate. Cells from day 3 postplating were treated with 5 µM VM26 for 24 h followed by further incubation in VM26-free media. Time 0 was when the drug was added to the media.

Preparation of Monoclonal Antibodies:

Monoclonal antibodies against GP46 were prepared by the method described in Cates et al., (1984) *J. Biol. Chem.* 259:2646–2650. Affinity purified ConA binding glycoproteins from L6 myoblast cells were injected into mice. Spleenn cells from immunized BALB/c mice were fused with NS-1 cells. Hybridomas producing anti-GP46 antibodies were screened by ELISA and Western Blot. The hybridomas producing anti-GP46 antibodies were grown in IMDM supplemented with 10% fetal calf serum. Antibodies from the spent media were used in the experiments.

Gel Electrophoresis and Immunoblotting:

At time 0, 3, 6, 18, 24, 48, 72, and 96 h, cells floating in the media and attached cells were collected in 0.1% SDS and boiled for 2 min. Protein levels were determined by the method of Lowry et al., (1951) *J. Biol. Chem.* 193:265–275. 70 µg of protein were separated on an 8.5% SDS-polyacrylamide gel and electrophoresis was performed as described in Laemmli (1970) *Nature* 227:680–685. The protein samples were transferred onto nitrocellulose paper by Western Blotting for 1.5 h at 100 Volts. Blots were blocked with 3% casein in Tris buffer for 1 h. GP46 was tagged by incubating overnight with 0.2 µg/ml of mouse anti-GP46 monoclonal antibodies. Unbound antibodies were washed out with Tris buffer. Bound antibodies were detected by incubating 1 h with 0.2 µCi/10 mL of $^{125}$I-rabbit anti-mouse IgG and visualized by exposing to X-ray film. The resulting GP46 protein bands that appeared on the X-ray film were scanned by a laser densitometer to quantitate results.

Figure 1B:
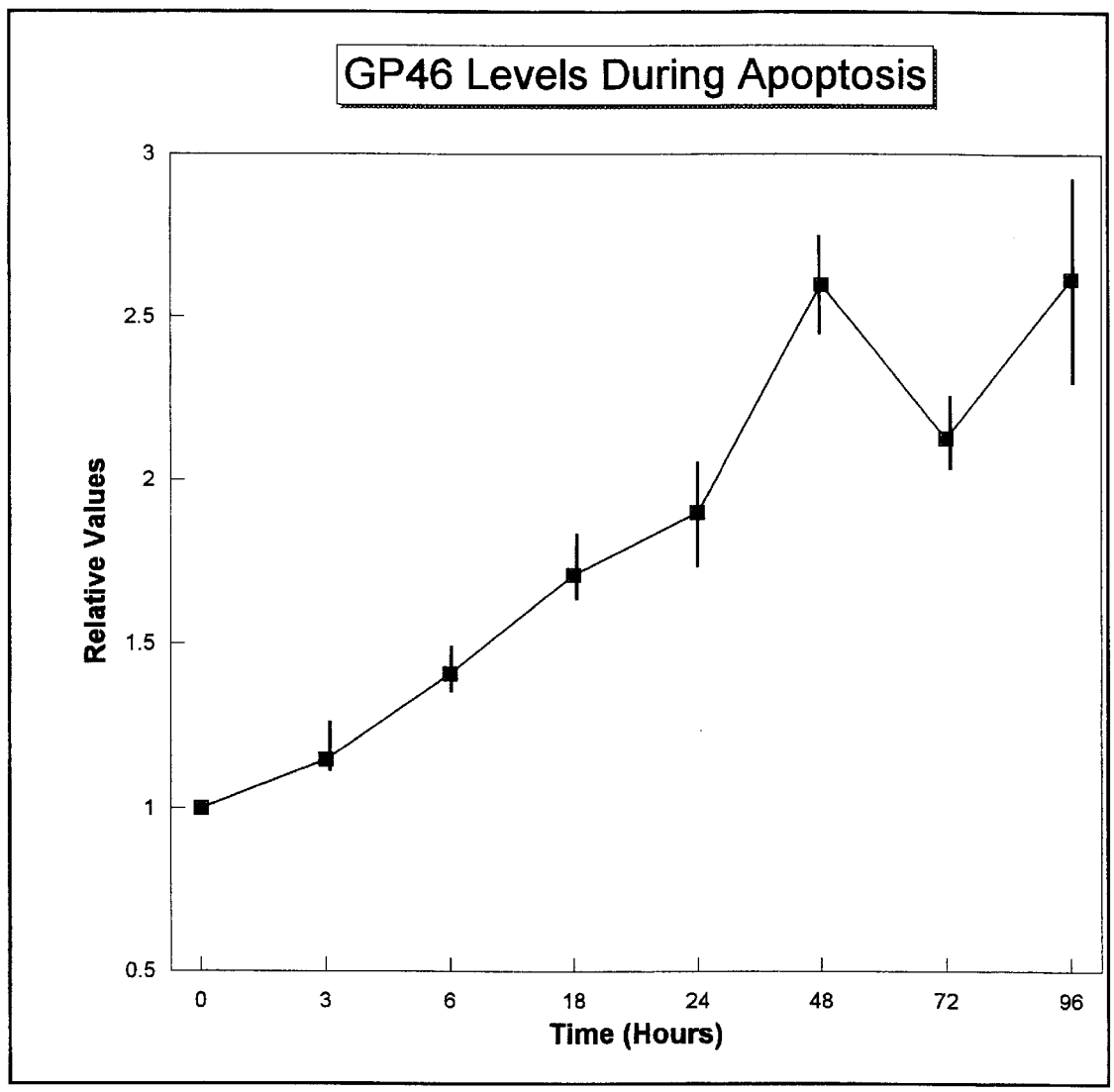

The results presented in FIG. 1 demonstrate that the amount of GP46 increases several fold over time after the addition of VM26, which acts as a chemical signal known to induce apoptosis. GP46 amounts remain high even 96 h after signalling into this pathway. In fact, the amount of GP46 begins to increase coincidental with the appearance of large DNA breaks at 6 h, indicating that apoptosis has begun (See Desjardins and MacManus (1995) *Exp. Cell Res.* 216:380–387, FIG. 4A). The amount of GP46 doubles by 48 h, at which time the DNA ladder, a hallmark of apoptosis, has appeared (See Desjardins and MacManus, supra, FIG. 4B). These results indicate that levels of GP46 increase significantly upon induction of apoptosis. GP46 levels increase at the start of apoptosis and reach a maximum level at the end of the apoptotic cell death process.

EXAMPLE II

Demonstration that Levels of GP46 Increase During Apoptosis

Treatment of HT29 cells with VM26:

Experiments were carried out by subculturing HT29 at a density of $2.5 \times 10^6$ cells in 10 ml DME per 100-mm plate. Cells from day 3 postplating were treated with 5 µM VM26 for 24 h followed by further incubation in VM26-free media for 24 h.

Labeling of Cells:

Cells were fixed with 3% paraformaldehyde in PBS and permeabilized with 0.1% Triton -X100 in PBS for 4 min. Fixed cells were incubated and labeled with anti-GP46 antibodies (75 µg/mL) for 20 min. at room temperature. Cells were washed four times for 5 min. with PBS and incubated with rhodamine-conjugated rabbit anti-mouse IgG (75 µg/ml) for 20 minutes. Cells were washed 4 times for 5 minutes with PBS.

Phase-Contrast Microscopy and Immunofluorescence Microscopy:

Cells were examined with a Zeiss photomicroscope provided with an epifluorescence attachment and phase-contrast condenser.

Figure 2A:
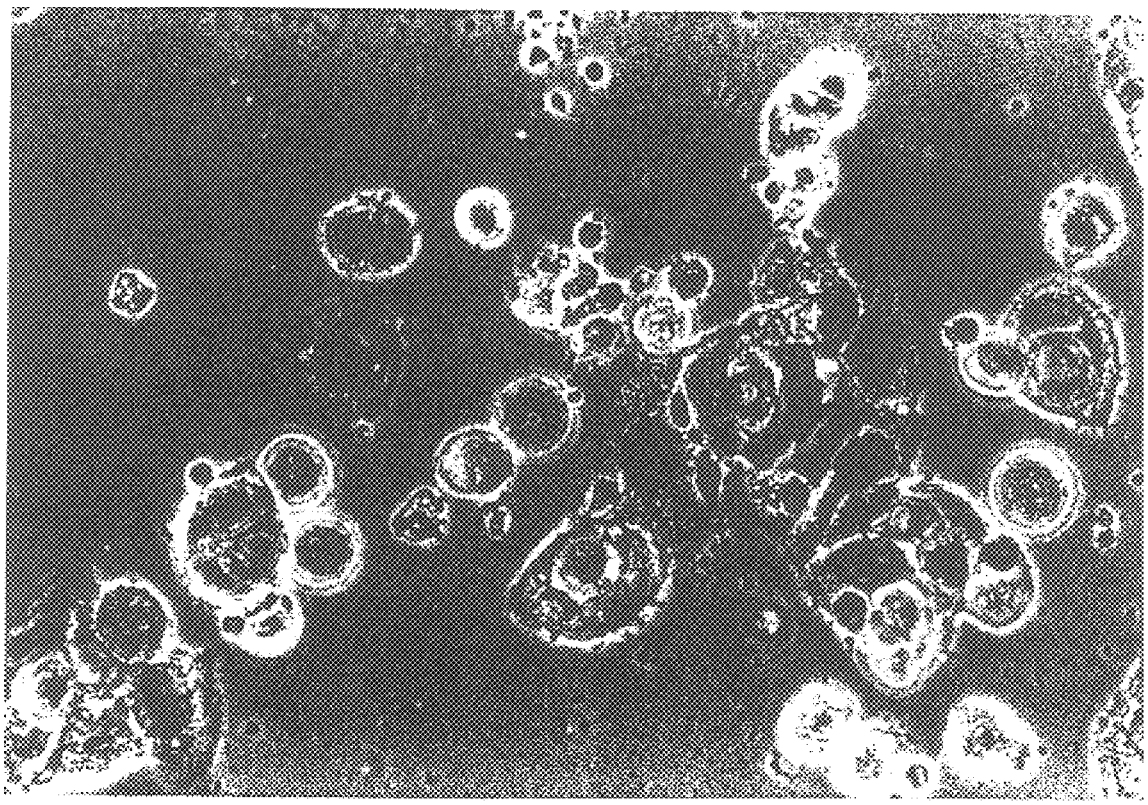
FIG. 2 shows the phase-contrast microscopy and immunofluorescence of HT29 cells treated with VM26 and labeled with anti-GP46 antibodies. HT29 cells were treated with 5 $\mu$M VM26 for 24 h followed by a further incubation without VM26 as described in Desjardins and MacManus (1995) *Exp. Cell Res.* 216:380–387. Cells were labeled with anti-GP46 antibodies and visualized by staining with rabbit anti-mouse IgG conjugated with rhodamine. Panel A is a picture of HT29 cells taken under a phase-contrast microscope. Panel B is a picture of the same frame under immunofluorescence light.
Figure 2B:
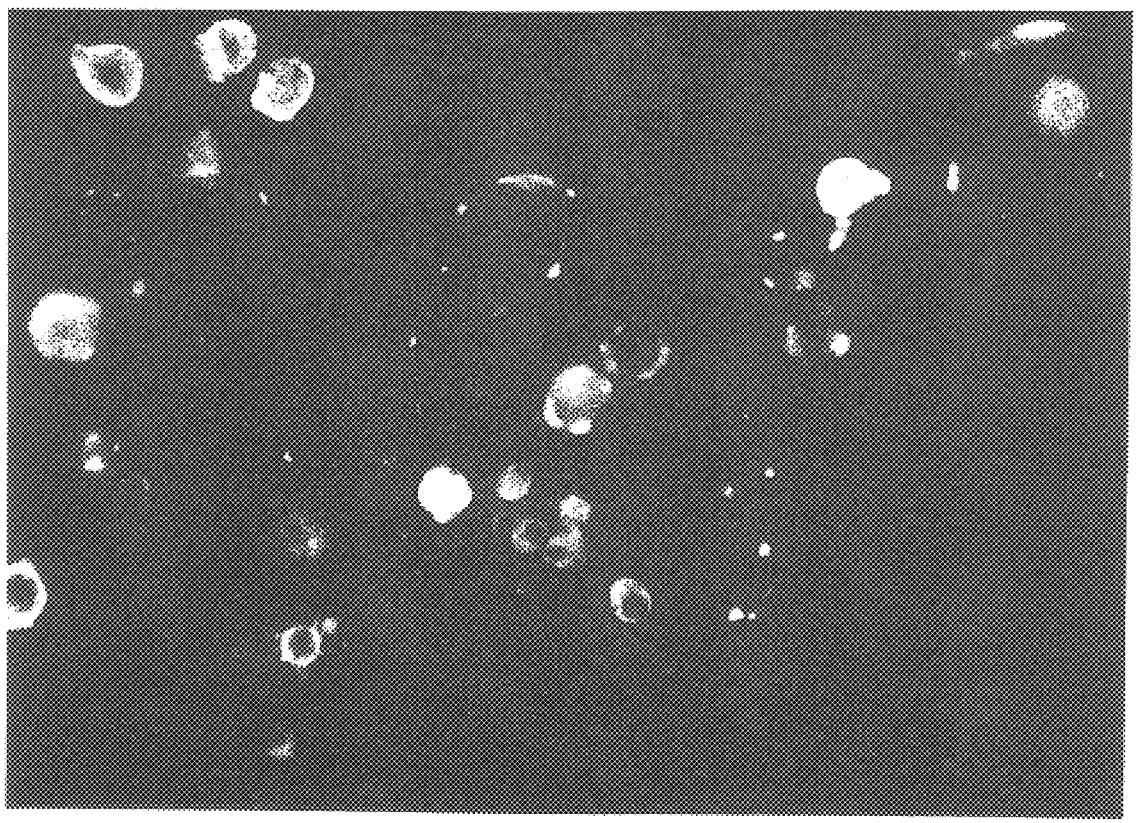

The results presented in FIG. 2A show a phase-contrast microscope frame of HT29 cells at 48 h after the addition of VM26. One can observe morphologically cells at different stages of apoptosis in the same mixture. There are "swelling" cells (second stage), early and late detaching and "rounding" cells (third stage) and shruken, dead "floating" cells (fourth stage) (See Desjardins and MacManus (1995) *Exp. Cell Res.* 216:380–387). FIG. 2B represents the same frame observed under immunofluorescent light. By comparing FIG. 2A and 2B, one can observe that GP46 is present in very low amounts in the swelling cells, much higher amounts in the rounding cells, and the highest amounts in shrunken floating cells. These results also coincide with the appearance of large DNA breaks and the DNA ladder (Desjardins and MacManus, supra). Over time, the proportion of cells at later stages of apoptosis increases, therefore, the amount of GP46 in the total cell population also increases as reflected in FIG. 1.

These results clearly shown that GP46 increases upon induction of apoptosis and that anti-GP46 antibodies serve both as an early marker of cells undergoing apoptosis and as a marker for determining if cells have died by apoptosis.

I claim:

1. A method of detecting the presence of apoptosis in a cellular, tissue, extract or homogenate sample, comprising
   (a) reacting said sample with an antibody or fragment thereof for a time and under conditions sufficient to allow binding of said antibody or fragment thereof with GP46 in said sample, wherein said antibody or fragment thereof is immunoreactive with affinity purified ConA binding glycoproteins and wherein said GP46 is also known as HSP47 or colligin; and
   (b) detecting the presence of immune complexes formed between said antibody or fragment thereof and GP46 in said sample, wherein the presence of said immune complexes in said sample is correlated with the presence of apoptosis in said sample.

2. The method of claim 1, wherein said antibody of fragment thereof is a monoclonal antibody.

3. The method of claim 2, wherein said monoclonal antibody is prepared by injecting affinity purified ConA binding glycoproteins from rat myoblast cells into mice, fusing spleen cells from said mice with NS-1 cells, screening for hybridomas producing anti-GP46 antibodies, and obtaining antibodies from said hybridomas.

4. The method of claim 1, wherein said sample is obtained from a human subject.

5. The method of claim 1, wherein said antibody or fragment thereof is detectably labeled.

6. The method of claim 5, wherein said label is detected by chemiluminescence, radioimmunoassay, immunofluorescence, colorometric analysis or spectrophotometry.

7. The method of claim 1, wherein said immune complex is detected by incubation with a labeled anti-species antibody which is immunoreactive with said antibody or fragment thereof.

8. A method of detecting sites of apoptosis in a patient, comprising
   (a) preparing a labeled antibody or fragment thereof, wherein said antibody or fragment thereof is immunoreactive with affinity purified ConA binding glycoproteins and wherein said label is a medically useful label;
   (b) administering a safe and effective amount of said labeled antibody or fragment thereof to the patient; and
   (c) detecting the presence of immune complexes formed between said antibody or fragment thereof and GP46 in said patient and wherein said GP46 is also known as HSP47 or colligin, wherein the presence of said immune complexes in said sample is correlated with sites of apoptosis in said patient.

9. The method of claim 8, wherein said antibody or fragment thereof is a monoclonal antibody.

10. The method of claim 9, wherein said monoclonal antibody is prepared by injecting affinity purified ConA binding glycoproteins from rat myoblast cells into mice, fusing spleen cells from said mice with NS-1 cells, screening for hybridomas producing anti-GP46 antibodies, and obtaining antibodies from said hybridomas.

11. The method of claim 8, wherein said administering is by at least one method selected from the group consisting of intradermal, subcutaneous, intramuscular, intraperitoneal and intravenous injection.

12. The method of claim 8, wherein said immune complexes are detected by gamma scintigraphy, emission computed tomography or single photon emission computed tomography.

13. The method of claim 8, wherein said label is a radionuclide.

14. The method of claim 13, wherein said radionuclide is iodine.

15. The method of claim 8, wherein the presence of said immune complexes is determined on a macroscopic scale at the time of surgical exploration.

* * * * *